United States Patent
Hansson

[11] Patent Number: 6,036,491
[45] Date of Patent: Mar. 14, 2000

[54] SCREW THREAD IMPLANT

[75] Inventor: Stig Hansson, Askim, Sweden

[73] Assignee: Astra Aktiebolag, Sodertalje, Sweden

[21] Appl. No.: 08/809,261
[22] PCT Filed: Feb. 12, 1997
[86] PCT No.: PCT/SE97/00212
   § 371 Date: Mar. 13, 1997
   § 102(e) Date: Mar. 13, 1997
[87] PCT Pub. No.: WO97/29713
   PCT Pub. Date: Aug. 21, 1997

[30] Foreign Application Priority Data

Feb. 13, 1996 [SE] Sweden .................................. 9600517

[51] Int. Cl.⁷ .................................................. A61C 8/00
[52] U.S. Cl. .......................................................... 433/174
[58] Field of Search ................................ 433/174; 606/73

[56] References Cited

U.S. PATENT DOCUMENTS

| | | | |
|---|---|---|---|
| 4,177,524 | 12/1979 | Grell et al. ................................. | 606/73 |
| 4,760,843 | 8/1988 | Fischer et al. ............................. | 606/73 |
| 4,957,437 | 9/1990 | Shimura et al. ........................ | 433/174 |
| 5,269,685 | 12/1993 | Jorneus et al. ........................... | 433/174 |
| 5,571,139 | 11/1996 | Jenkins, Jr. ................................ | 606/73 |
| 5,816,813 | 10/1998 | Hansson et al. ......................... | 433/174 |

FOREIGN PATENT DOCUMENTS

| | | | |
|---|---|---|---|
| 230 678 | 8/1987 | European Pat. Off. ............... | 433/174 |
| 9306786 | 4/1993 | WIPO .................................... | 433/174 |
| 94/07428 | 4/1994 | WIPO .................................... | 433/174 |

*Primary Examiner*—Nicholas D. Lucchesi
*Attorney, Agent, or Firm*—White & Case, LLP

[57] ABSTRACT

The present invention relates to a thread or oriented macroroughness for bone implants, particularly threaded dental implants, a section of said thread or roughness (i.e. the profile) comprising two flanks, a top radius R at the apex formed by the intersection of said two flanks, a bottom radius r formed at the bottom of the groove between two adjacent threads or roughnesses, said flanks forming an angle v with a plane which is perpendicular to a cross-section of said thread or roughness and perpendicular to the surface of the implant body, said profile further having a height D. According to the invention the dimensions of the thread or roughness are subject to the following restrictions: for $10° \leq v < 35°$, R is greater than 0.4×D and that, for $35° \leq v < 55°$, R is greater than 0.2×D. In a preferred embodiment the restrictions are: for 0.05 mm≦D≦0.5 mm and $35 \leq v \leq 55°$, the top radius R is larger than 0.2×D but smaller than D, and in that, for 0.25 mm≦D≦0.5 mm and $10° \leq v < 35°$, R is greater than 0.4×D but smaller than D. FIG. 1.

25 Claims, 6 Drawing Sheets

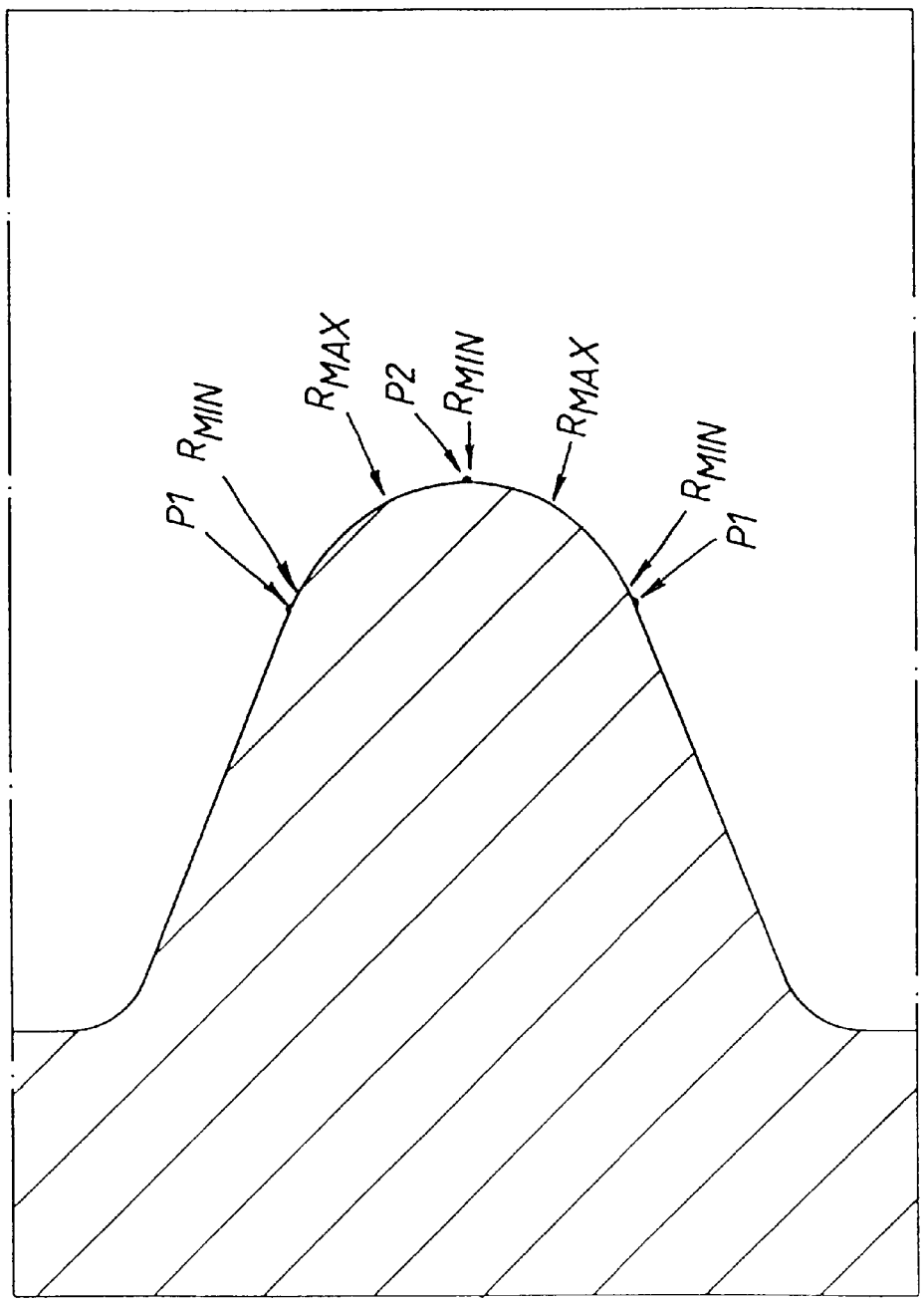

SCREW THREAD IMPLANT

The present invention relates to implants for implantation into bone, in particular to dental implants, said implants being provided with threads or an oriented macroroughness. The term "oriented macroroughness" should be understood to comprise elongated beads which may be continuous or not, which may be oriented along the periphery of a cross-section of the implant or not. The oriented macroroughness should have a cross-section or profile specified in the way the thread profile will be defined below and in the appended claims.

BACKGROUND OF THE INVENTION

Bone implants are normally made of rigid material, mostly of titanium, which has been shown to have an affinity for bone tissue and which has an excellent biocompability. Bone implants often have a cylindrical, threaded shape and are screwed into bore-holes in the bone tissue which may be pre-tapped or not.

Under certain conditions titanium implants attain a close apposition with the bone tissue which sometimes is called osseointegration. Some factors determining the tissue response to a bone implant have been found to be the following: the biocompatibility of the implant material, the implant design, the implant surface, the status of the host bed, the surgical technique and the loading conditions. As far as the implant design is concerned, a review of the dental implant literature reveals that implants of a large number of different shapes have been used in the past. It appears as if new implant designs to a great extent have been introduced and evaluated on a trial and error basis. As the reason for an implant failure is multi-factorial, a good design may have been discarded due to for example an improper surgical technique or improper loading conditions. Titanium screw-shaped dental implants were used early in the 1960's, those implants do not appear to have been a success; possibly due to the reasons mentioned above.

Overloading has been identified as a main etiologic factor behind loss of dental implants today. If bone is subject to extreme stress it will be resorbed. Assuming that stress induced bone resorbtion is triggered off when the stresses reaches a certain level, an implant should have such a design that the maximum stresses arising in the bone, as a result of a certain load, is minimized.

Screw-shaped titanium dental implants dominate the market today. Several studies have addressed the relation between macroscopic design and holding power of screws in bone. By far most of them have been made within the orthopaedic discipline and have had an experimental approach. Pullout tests were carried out in the 1950's on dog femurs and tibias using vitallium bone screws with different thread profiles. It was observed that when pulling out a freshly inserted screw, the bone threads did not strip but the screw pulled out a small cone-shaped button of compact bone. Clinical experience shows that a bone plate and its screws are sometimes avulsed from bone. This avulsion is preceded by bone resorbtion. The opinion has been expressed that such a loss of holding power is caused by mechanical factors. Continuous compression of cancellous bone by screw threads has been shown to result in hypertrophy and realignment of the trabeculae in parallell with the force. It has also been claimed that cortical bone subjected to compression retains its integrity and is not resorbed.

The relevance of pull-out experiments can however be doubted. In a pull-out test acute fracture is provoked. Dental implants seldom fail by acute fracture of the supporting bone. On the contrary the fracture of the implant-bone interface is normally the end of a long process of marginal bone resorbtion. As mentioned above, the assumption that stress induced bone resorbtion is triggered off when the stresses reaches a certain level implies that an implant should be given such a design that the stress peaks arising in the bone are minimized.

It has been found that a bone implant being provided with threads or an oriented macro-roughness intended to transfer loads to the bone tissue and designed in accordance with the appended main claim minimizes the stress peaks in the surrounding bone tissue. Preferred embodiments are set forth in the dependent claims.

SHORT DESCRIPTION OF THE APPENDED DRAWINGS

FIG. 7 illustrates an alternative embodiment of the apex of the thread.

DETAILED DESCRIPTION OF A PREFERRED EMBODIMENT OF THE INVENTION

Figure 1:
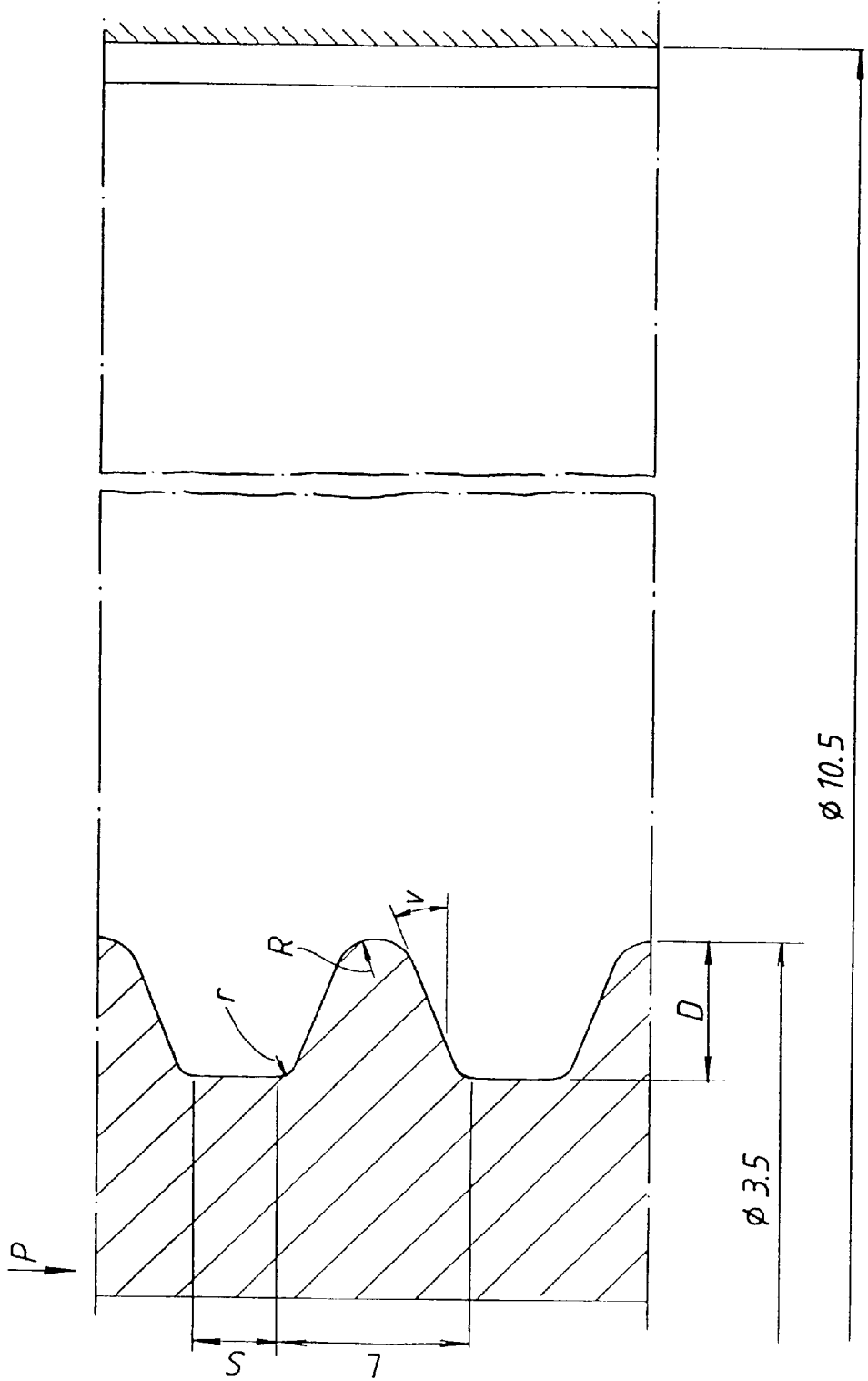
FIG. 1 illustrates a profile of a thread or roughness according to the invention.

FIG. 1 illustrates how the parameters describing the profile according to the invention are defined. The implant shown is a screw-shaped dental implant with a diameter of 3.5 mm.

The thread profile has two thread flanks and the height of the thread is D. The top radius formed at the apex of the thread profile at the intersection of the two thread flanks is designated R, and the bottom radius between two adjacent thread profiles r. The thread flanks form an angle v with a plane which is perpendicular to a cross-section of the thread and perpendicular to the surface of the implant body. The distance L is defined as the distance between the points of intersection between the two flanks on a thread and the surface of the implant body, the surface of the implant body being defined as the cylindrical surface touching the deepest parts of the threads.

A standard prior art screw-shaped implant with an overall diameter of 3.5 mm would typically be provided with threads having a height D of about 0.35 mm, a flank angle v of 30°, a top radius R of about 0.065 mm corresponding to about 0.2×D and bottom radius of about 0.05 mm corresponding to about 0.1 5×D.

As discussed above, the object of the invention is to equalize and mimimize the stress concentrations in the bone tissue which are a result of the loads on the implant in order to obtain an even stress distribution in the bone tissue so as to avoid resorption of the bone tissue because of high stress concentrations whilst avoiding low stresses that also might cause bone tissue resorption.

In accordance with the invention it has been found that screw threads (macro-roughness) either having a top radius exceeding 0.4×D or a flank angle exceeding 35° substantially equalizes the stress distribution in the bone tissue surrounding the implant. More particularly, the top radius R should be larger than 0.2×D and smaller than D for 35°≦v≦55° and 0.05≦D≦0.5 mm and larger than 0.4×D and smaller than D for 10°≦v<35° and 0.25≦D ≦0.5 mm.

An embodiment which at present seems most promising is an embodiment wherein 0.03≦R≦0.05 mm, 37°≦v≦43°, 0.01≦r≦0.025 and 0.08≦D≦0.15.

The following calculations illustrate this point. The calculations are performed by means of finite element analysis. The theory of elasticity according to Timoshenko is applied. The program used is Ansys revision 5.0.

Figure 2:
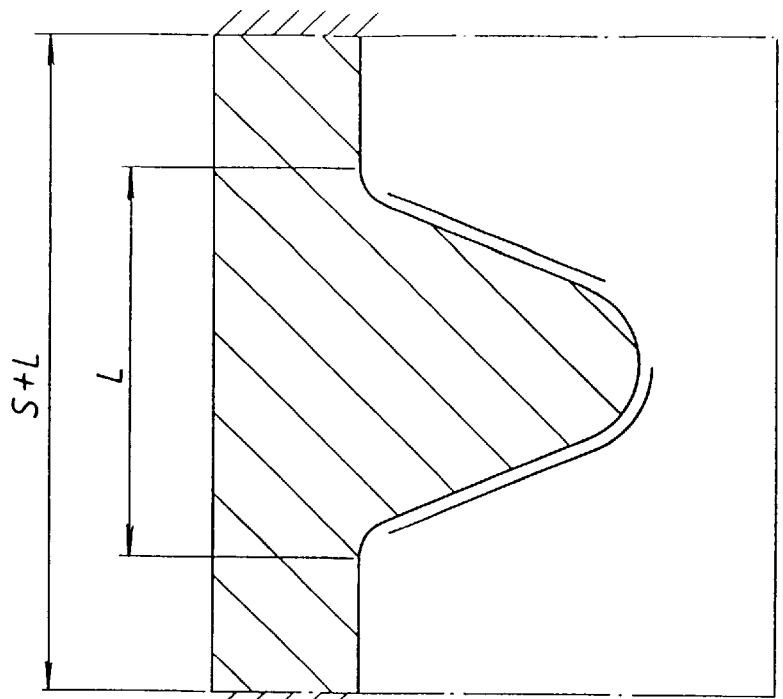
FIG. 2 illustrates the so called contact elements on the profile.
Figure 6:
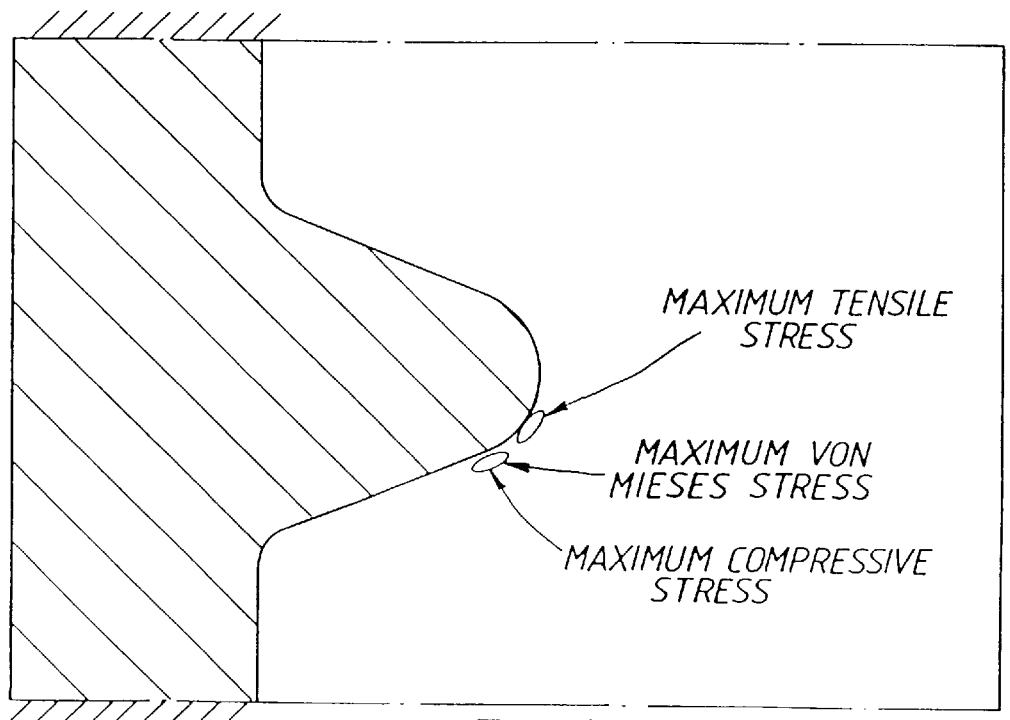
FIG. 6 illustrates the location of the different maximal stresses.

The object studied is a vertically oriented screw-like implant with a major diameter of 3.5 mm. This implant is built up of identical axisymmetric elements where each element corresponds to one pitch height of a screw. The thread is modeled as a ring on each element. The profile of the thread as seen in FIG. 1 is characterized by the thread depth (D), the top radius (R), the flank angle (v), the bottom radius (r) and a straight part of the length S at the bottom of the thread. The length of the curved part of such an element is, as defined above, designated L. The straight part of the length (S) was set as a coefficient c multiplied with this length (S=c·L ). Calculations were made for values of the thread depth of 0.1 mm, 0.2 mm, 0.3 mm and 0.4 mm while the value of the top radius was set as a coefficient multiplied with the thread depth. The value of this coefficient was set at 0.1, 0.2, 0.4, 0.6, 0.8 and 1. The flank angle was varied between 0° and 60° with an increment of 10°. The bottom radius was set at 0.1 times the thread depth. The coefficient c was set at 0, 0.2, 0.4, 0.8 and 1.6. This means that a total of 4×6×7×5×1=840 different thread profiles are used. The implant was assumed to be infinitely long and was assumed to be completely embedded in cortical bone. 100% bone apposition was assumed. The bone was assumed to be attached to the inner wall of an outer cylinder with a diameter of 10.5 mm, see FIG. 1. Rotational symmetry was further assumed. The implant and the outer cylinder were assumed to be infinitely stiff while the bone was assumed to be a continuum material, isotropic and linearly elastic with a modulus of elasticity (Young's modulus) of 150 GPa and a Poisson's ratio amounting to 0.3. It was assumed that the bone-implant interface was frictionless and that only compressive forces could be transmitted between the implant and the bone. These interface conditions are modeled by means of contact elements, the lines adjacent to the thread surface in FIG. 2. As is evident from FIG. 2 parts of the interface does not have contact elements, the reason being that the interfacial bone at these locations in test runs had turned out to retreated from the implant.

Figure 3:
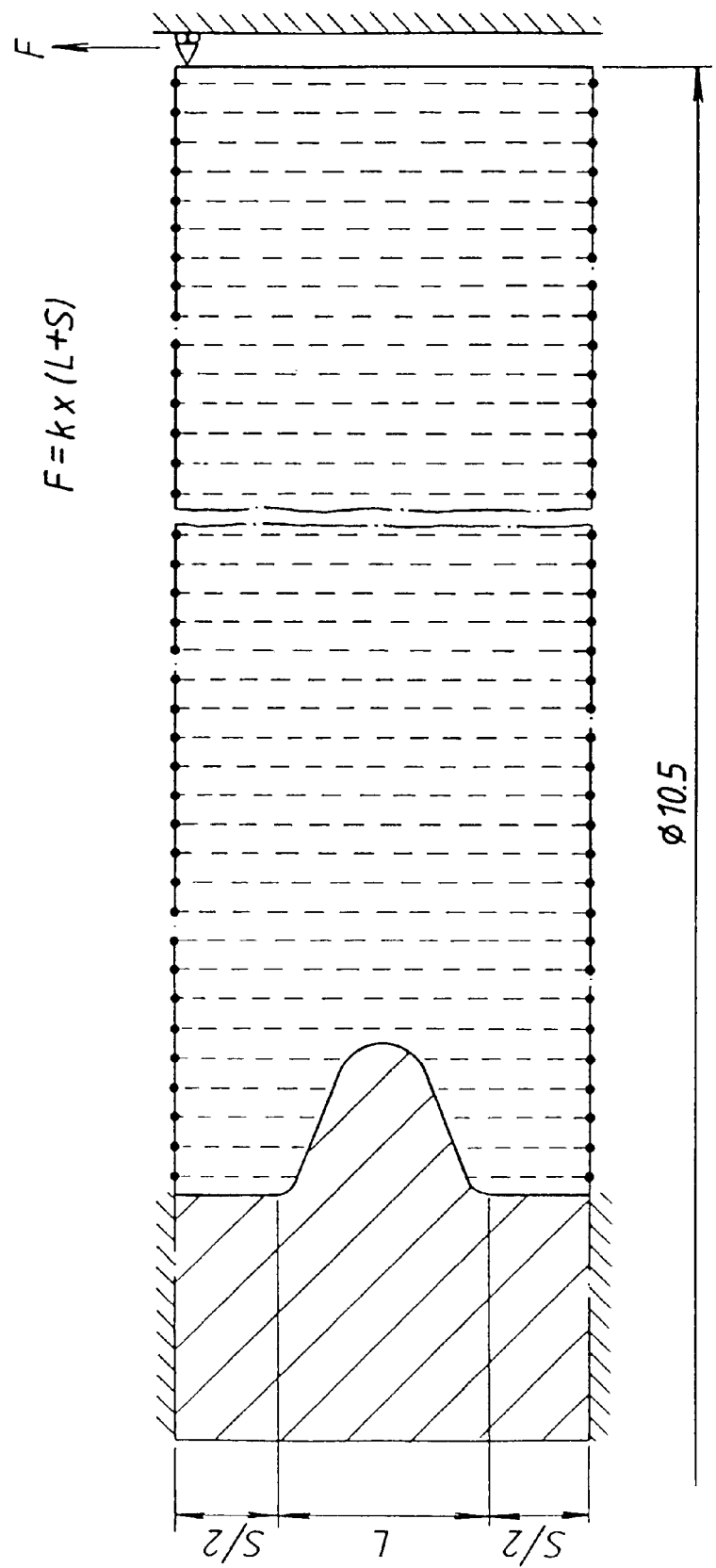
FIG. 3 illustrates the model used to calculate the stresses.

An infinitely big axial load (a finite load per screw element) was applied on the infinitely long implant. With the assumptions made, the same mechanical events (stresses, strains, displacements) will occur in the bone outside all elements of which the infinitely long implant is composed. Consequently it is sufficient to study one single element of the implant, including the surrounding bone, provided that proper boundary conditions can be set up wherein this element with its surrounding bone borders to the overlying and underlying counterparts. The boundary conditions which were used were that, when the load was applied, all nodes in the bone lying in the horizontal plane defined by the upper limiting surface of the element in couples underwent the same displacements as the corresponding nodes in the bone lying in the horizontal plane defined by the lower limiting surface of the same element (FIG. 3).

The load, F, which was transmitted from the implant element into the bone tissue was set as a constant (k) multiplied with the length (L+S) of the implant element which latter was dependent upon the top radius, the flank angle, the bottom radius, the thread depth and the length of the straight part if any. The information seeked was the maximum tensile stress, the maximum compressive stress and the maximum von Mieses stress in the bone as a function of the values of the variables used. The implant element was modeled to be completely stiff and fixed, the load F being applied at the further end of the bone as is shown in FIG. 3.

Figure 4:
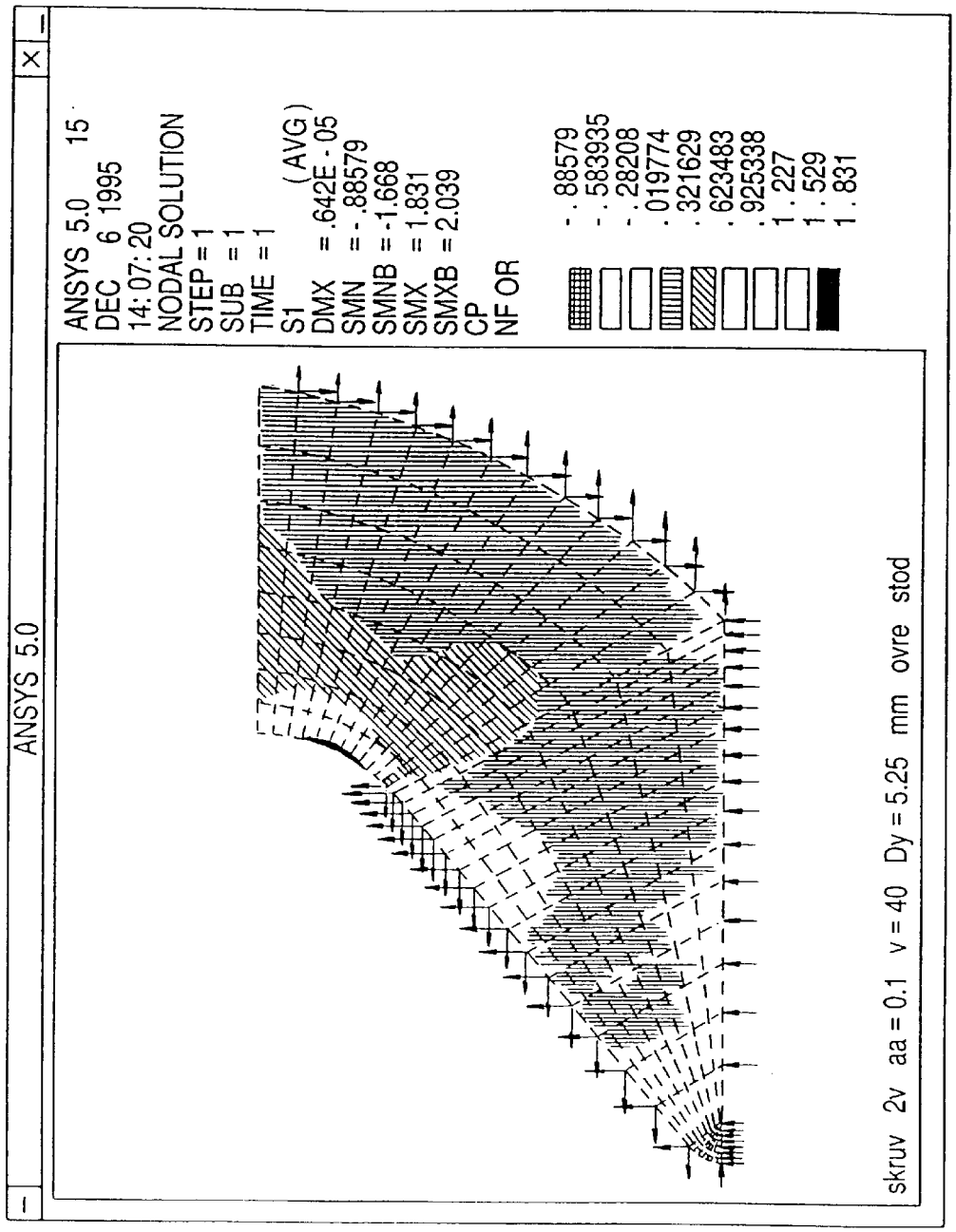
FIGS. 4 and 5 show the distribution of the elements around the profile of a profile according to the invention respectively a prior art implant.
Figure 5:
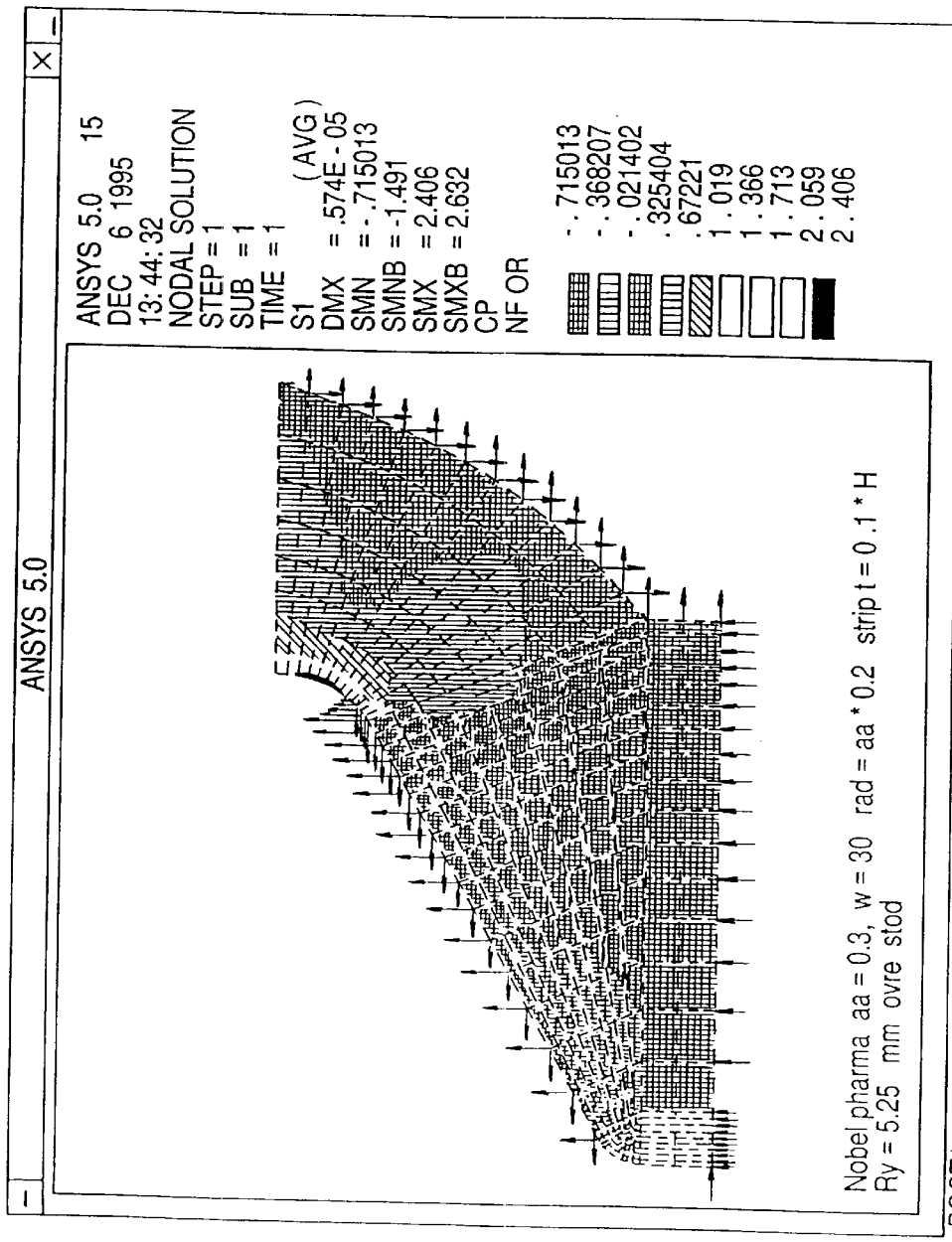

The element mesh was built up parametrically. In FIG. 4 and 5 the element mesh close to the implant is shown for two calculation examples called Parameter set 1 and Parameter set 2. Parameter set 1 corresponds to a thread profile according to the invention with D=0.1 mm, v=40° and R=0.4×D, r=0.1×D whereas parameter set 2 largely corresponds to the prior art implant given above. Each element contained four nodes, the number of degrees of freedom for each node being two. The number of elements used in the mesh varied with the length of the straight portion at the bottom of the thread expressed by the coefficient c. With a value of the coefficient c of 0, 0.2–0.4 and 0.8–1.6 the number of elements were 1129, 1305 and 1481 respectively.

It is assumed that the screw-like structure was embedded in cortical bone. The following mean values for the ultimate stress of human cortical bone have been obtained empirically: $\sigma_{u0}^+$=133 MPa, $\sigma_{ou}^-$=193 MPa, $\sigma_{u90}^+$=51 MPa and $\sigma_{u90}^-$=133 MPa where the ultimate stress in regard of tension and compression is denoted by $\sigma_u^+$ and $\sigma_u^-$ respectively, $\sigma_{u0}$ and $\sigma_{u90}$ signify ultimate stresses in parallell with the long axis of the bone respectively in a transversal plane. It is natural to allow bone stresses of different kinds in proportion to the ultimate stress. The ratios $\sigma_{u0-}/\sigma_{u0}^+$ and $\sigma_{u90-}/\sigma_{u90}^+$ are according to the above 1.45 and 2.61 respectively. In order to simplify comparisons with the maximum tensile stresses obtained the ratios $\sigma_{max-}/1.45$ and $\sigma_{max-}/2.61$ are presented in the results (tables 1–4 and 9–12). However, for the calculations, the ratio $\sigma_{max-}/2$ is the value which is of most interest.

Disregarding the von Mieses stress, the combination of values of the profile parameters which minimizes the highest of the values, $\sigma^+_{max}$ and $\sigma_{max-}/2$ may be regarded as the most favourable thread design.

The von Mieses stress can be expressed by the formula $$\sigma_e = \sqrt{\sigma_1^2 + \sigma_2^2 + \sigma_3^2 - \sigma_1\sigma_2 - \sigma_2\sigma_3 - \sigma_1\sigma_3}$$

where $\sigma_1$, $\sigma_2$ and $\sigma_3$ are the principal stresses. This formula does not take into consideration a situation where the compressive stress of a material differs from the tensile stress. An analysis of the results showed that the maximum von Mieses stress regularly was composed of one high compressive principal stress, one compressive stress of intermediate magnitude and one insignificant tensile principle stress. In order to be directly comparable with the maximum tensile stress the maximum von Mieses stress should, as the maximum compressive stress, be divided with a certain factor. It is obvious that the value of this factor lies between 1.45 and 2.61 (it never attains the value 1.45 nor does it attain the value 2.61). For that reason the ratios $\sigma_{e.max}/1.45$ and $\sigma_{e.max}/2.61$ are presented in the results in tables 1–4 and 9–12 below. The von Miese's stresses are given for comparative purposes.

Tables 1–4 show the results of the calculations. As can be seen in in the tables, the values for $\sigma^+_{max}$ generally are less than 2 and for σmax–/1.45 generally are less than 2.75

(which corresponds to a value also less than 2 for $\sigma_{max}-2$) within the rectangles which are drawn with dashed lines in table 1 only but are to correspond to the fields 0.05 mm≦D≦0.5 mm and 35≦v≦55°, the top radius R being larger than 0.2×D but smaller than D; 0.25 mm≦D≦0.5 mm and 10°≦v<35°, R being greater than 0.4×D but smaller than D. The calculation results for the parameter fields in which $\sigma^+_{max}<2$ and $\sigma_{max\_}/2<2$ are illustrated with full lines in the tables.

As clearly can be seen, the standard screw-shaped implant falls outside these parameter fields.

Tables 5–8 illustrate the effect obtained by the introduction of a distance S between two adjacent threads. The part of the distance S which is straight is given as a coefficient to be multiplied with the length L, i. e. the distance defined above between the points where the flanks intersect the body of the implant. If the coefficient is 0 there is no positive effect of the introduction of a straight part. As can be seen, the positive effects mainly occur for small flank angles and for relatively large top radii, the parameter fields being shifted slightly to lower top radii for small flank angles as for instance can be seen by comparing tables 3 and 11.

Tables 9–12 show the minimum values for $\sigma^+_{max}$ and the corresponding $\sigma_{max}^-/1.45$ corresponding to the values given in tables 5–8.

Some preferred embodiments are given in the following lists.

| | Top radius | Flank angle | Bottom radius | Thread height(D) | Straight part at bottom |
|---|---|---|---|---|---|
| 1 | 0.03–0.05 | 37°–43° | 0.01–0.025 | 0.08–0.15 | 0 |
| 2 | 0.2D–1.0D | 35°–55° | 0–0.2D | 0.05–0.15 | 0 |
| 3 | 0.2D–1.0D | 35°–55° | 0–0.2D | 0.05–0.15 | 0–1D |
| 4 | 0.2D–1.0D | 35°–55° | 0–0.2D | 0.05–0.15 | 1D–2D |
| 5 | 0.2D–1.0D | 35°–55° | 0–0.2D | 0.15–0.25 | 0 |
| 6 | 0.2D–1.0D | 35°–55° | 0–0.2D | 0.15–0.25 | 0–1D |
| 7 | 0.2D–1.0D | 35°–55° | 0–0.2D | 0.15–0.25 | 1D–2D |
| 8 | 0.2D–1.0D | 35°–55° | 0–0.2D | 0.25–0.35 | 0 |
| 9 | 0.2D–1.0D | 35°–55° | 0–0.2D | 0.25–0.35 | 0–1D |
| 10 | 0.2D–1.0D | 35°–55° | 0–0.2D | 0.25–0.35 | 1D–2D |
| 11 | 0.2D–1.0D | 35°–55° | 0–0.2D | 0.35–0.50 | 0 |
| 12 | 0.2D–1.0D | 35°–55° | 0–0.2D | 0.35–0.50 | 0–1D |
| 13 | 0.2D–1.0D | 35°–55° | 0–0.2D | 0.35–0.50 | 1D–2D |
| 14 | 0.2D–1.0D | 35°–55° | 0.2D–1.0D | 0.05–0.15 | 0 |
| 15 | 0.2D–1.0D | 35°–55° | 0.2D–0.8D | 0.05–0.15 | 0–1D |
| 16 | 0.2D–1.0D | 35°–55° | 0.2D–0.6D | 0.05–0.15 | 1D–2D |
| 17 | 0.2D–1.0D | 35°–55° | 0.2D–1.0D | 0.15–0.25 | 0 |
| 18 | 0.2D–1.0D | 35°–55° | 0.2D–0.8D | 0.15–0.25 | 0–1D |
| 19 | 0.2D–1.0D | 35°–55° | 0.2D–0.6D | 0.15–0.25 | 1D–2D |
| 20 | 0.2D–1.0D | 35°–55° | 0.2D–1.0D | 0.25–0.35 | 0 |
| 21 | 0.2D–1.0D | 35°–55° | 0.2D–0.8D | 0.25–0.35 | 0–1D |
| 22 | 0.2D–1.0D | 35°–55° | 0.2D–0.6D | 0.25–0.35 | 1D–2D |
| 23 | 0.2D–1.0D | 35°–55° | 0.2D–1.0D | 0.35–0.50 | 0 |
| 24 | 0.2D–1.0D | 35°–55° | 0.2D–0.8D | 0.35–0.50 | 0–1D |
| 25 | 0.2D–1.0D | 35°–55° | 0.2D–0.6D | 0.35–0.50 | 1D–2D |
| 26 | 0.2D–1.0D | 35°–55° | <0.85R | 0.05–0.15 | 0 |
| 27 | 0.2D–1.0D | 35°–55° | <0.85R | 0.05–0.15 | 0–1D |
| 28 | 0.2D–1.0D | 35°–55° | <0.85R | 0.05–0.15 | 1D–2D |
| 29 | 0.2D–1.0D | 35°–55° | <0.85R | 0.15–0.25 | 0 |
| 30 | 0.2D–1.0D | 35°–55° | <0.85R | 0.15–0.25 | 0–1D |
| 31 | 0.2D–1.0D | 35°–55° | <0.85R | 0.15–0.25 | 1D–2D |
| 32 | 0.2D–1.0D | 35°–55° | <0.85R | 0.25–0.35 | 0 |
| 33 | 0.2D–1.0D | 35°–55° | <0.85R | 0.25–0.35 | 0–1D |
| 34 | 0.2D–1.0D | 35°–55° | <0.85R | 0.25–0.35 | 1D–2D |
| 35 | 0.4D–0.6D | 10°–35° | 0–0.6D | 0.05–0.15 | 0 |
| 36 | 0.4D–0.6D | 10°–35° | 0–0.6D | 0.05–0.15 | 0–1D |
| 37 | 0.4D–0.6D | 10°–35° | 0–0.6D | 0.05–0.15 | 1D–2D |
| 38 | 0.4D–0.6D | 10°–35° | 0–0.6D | 0.15–0.25 | 0 |
| 39 | 0.4D–0.6D | 10°–35° | 0–0.6D | 0.15–0.25 | 0–1D |
| 40 | 0.4D–0.6D | 10°–35° | 0–0.6D | 0.15–0.25 | 1D–2D |
| 41 | 0.4D–0.6D | 10°–35° | 0–0.6D | 0.25–0.35 | 0 |
| 42 | 0.4D–0.6D | 10°–35° | 0–0.6D | 0.25–0.35 | 0–1D |
| 43 | 0.4D–0.6D | 10°–35° | 0–0.6D | 0.25–0.35 | 1D–2D |
| 44 | 0.4D–0.6D | 10°–35° | 0–0.6D | 0.35–0.50 | 0 |
| 45 | 0.4D–0.6D | 10°–35° | 0–0.6D | 0.35–0.50 | 0–1D |
| 46 | 0.4D–0.6D | 10°–35° | 0–0.6D | 0.35–0.50 | 1D–2D |
| 47 | 0.4D–0.6D | 10°–35° | 0.6D–1D | 0.05–0.15 | 0 |
| 48 | 0.4D–0.6D | 10°–35° | 0.6D–0.8D | 0.05–0.15 | 0–1D |
| 49 | 0.4D–0.6D | 10°–35° | 0.6D–1D | 0.15–0.25 | 0 |
| 50 | 0.4D–0.6D | 10°–35° | 0.6D–0.8D | 0.15–0.25 | 0–1D |
| 51 | 0.4D–0.6D | 10°–35° | 0.6D–1D | 0.25–0.35 | 0 |
| 52 | 0.4D–0.6D | 10°–35° | 0.6D–0.8D | 0.25–0.35 | 0–1D |
| 53 | 0.4D–0.6D | 10°–35° | 0.6D–1D | 0.35–0.50 | 0 |
| 54 | 0.4D–0.6D | 10°–35° | 0.6D–0.8D | 0.35–0.50 | 0–1D |
| 55 | 0.6D–1D | 10°–35° | 0–0.6D | 0.05–0.15 | 0 |
| 56 | 0.6D–1D | 10°–35° | 0–0.6D | 0.05–0.15 | 0–1D |
| 57 | 0.6D–1D | 10°–35° | 0–0.6D | 0.05–0.15 | 1D–2D |
| 58 | 0.6D–1D | 10°–35° | 0–0.6D | 0.15–0.25 | 0 |
| 59 | 0.6D–1D | 10°–35° | 0–0.6D | 0.15–0.25 | 0–1D |
| 60 | 0.6D–1D | 10°–35° | 0–0.6D | 0.15–0.25 | 1D–2D |
| 61 | 0.6D–1D | 10°–35° | 0–0.6D | 0.25–0.35 | 0 |
| 62 | 0.6D–1D | 10°–35° | 0–0.6D | 0.25–0.35 | 0–1D |
| 63 | 0.6D–1D | 10°–35° | 0–0.6D | 0.25–0.35 | 1D–2D |
| 64 | 0.6D–1D | 10°–35° | 0–0.6D | 0.35–0.50 | 0 |
| 65 | 0.6D–1D | 10°–35° | 0–0.6D | 0.35–0.50 | 0–1D |
| 66 | 0.6D–1D | 10°–35° | 0–0.6D | 0.35–0.50 | 1D–2D |
| 67 | 0.6D–1D | 10°–35° | 0.6D–1D | 0.05–0.15 | 0 |
| 68 | 0.6D–1D | 10°–35° | 0.6D–0.8D | 0.05–0.15 | 0–1D |
| 69 | 0.6D–1D | 10°–35° | 0.6D–1D | 0.15–0.25 | 0 |
| 70 | 0.6D–1D | 10°–35° | 0.6D–0.8D | 0.15–0.25 | 0–1D |
| 71 | 0.6D–1D | 10°–35° | 0.6D–1D | 0.25–0.35 | 0 |
| 72 | 0.6D–1D | 10°–35° | 0.6D–0.8D | 0.25–0.35 | 0–1D |
| 73 | 0.6D–1D | 10°–35° | 0.6D–1D | 0.35–0.50 | 0 |
| 74 | 0.6D–1D | 10°–35° | 0.6D–0.8D | 0.35–0.50 | 0–1D |
| 75 | 0.4D–0.6D | 10°–35° | <0.85R | 0.05–0.15 | 0 |
| 76 | 0.4D–0.6D | 10°–35° | <0.85R | 0.05–0.15 | 0–1D |
| 77 | 0.4D–0.6D | 10°–35° | <0.85R | 0.05–0.15 | 1D–2D |
| 78 | 0.4D–0.6D | 10°–35° | <0.85R | 0.15–0.25 | 0 |
| 79 | 0.4D–0.6D | 10°–35° | <0.85R | 0.15–0.25 | 0–1D |
| 80 | 0.4D–0.6D | 10°–35° | <0.85R | 0.15–0.25 | 1D–2D |
| 81 | 0.4D–0.6D | 10°–35° | <0.85R | 0.25–0.35 | 0 |
| 82 | 0.4D–0.6D | 10°–35° | <0.85R | 0.25–0.35 | 0–1D |
| 83 | 0.4D–0.6D | 10°–35° | <0.85R | 0.25–0.35 | 1D–2D |
| 84 | 0.4D–0.6D | 10°–35° | <0.85R | 0.35–0.50 | 0 |
| 85 | 0.4D–0.6D | 10°–35° | <0.85R | 0.35–0.50 | 0–1D |
| 86 | 0.4D–0.6D | 10°–35° | <0.85R | 0.35–0.50 | 1D–2D |
| 87 | 0.6D–1D | 10°–35° | <0.85R | 0.05–0.15 | 0 |
| 88 | 0.6D–1D | 10°–35° | <0.85R | 0.05–0.15 | 0–1D |
| 89 | 0.6D–1D | 10°–35° | <0.85R | 0.05–0.15 | 1D–2D |
| 90 | 0.6D–1D | 10°–35° | <0.85R | 0.15–0.25 | 0 |
| 91 | 0.6D–1D | 10°–35° | <0.85R | 0.15–0.25 | 0–1D |
| 92 | 0.6D–1D | 10°–35° | <0.85R | 0.15–0.25 | 1D–2D |
| 93 | 0.6D–1D | 10°–35° | <0.85R | 0.25–0.35 | 0 |
| 94 | 0.6D–1D | 10°–35° | <0.85R | 0.25–0.35 | 0–1D |
| 95 | 0.6D–1D | 10°–35° | <0.85R | 0.25–0.35 | 1D–2D |
| 96 | 0.6D–1D | 10°–35° | <0.85R | 0.35–0.50 | 0 |
| 97 | 0.6D–1D | 10°–35° | <0.85R | 0.35–0.50 | 0–1D |
| 98 | 0.6D–1D | 10°–35° | <0.85R | 0.35–0.50 | 1D–2D |

In preferred embodiments the distance between adjacent threads is smaller than 3D, preferably smaller than 2D.

In a further preferred embodiment the threads or macroroughness is combined with a microroughness having a pore size of 2 $\mu$ to 20 $\mu$, preferably 2 $\mu$ to 10 $\mu$. By such a combination of macroscopic and microscopic interlocking also implant surfaces which, if smooth, would not have interacted mechanically with the bone will take part in the transmission of the loads to the bone. This will further tend to smooth away the stress concentrations which inevitably will arise in the bone tissue due to the macroscopic interlocking and which the invention is to alleviate, thus further enhancing the effect the invention is intended to achieve. The microscopic roughness may for instance be made by blasting or chemical etching, but is preferably made by blasting with particles of $TiO_2$.

TABLE 1

Thread depth = 0.1 mm. No straight part at the bottom of the thread. The value of $\sigma^+_{max}$ for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given. The value of the top radius expressed as a coefficient multiplied with the thread depth (D).

| Flank angle | | Top radius | | | | | |
|---|---|---|---|---|---|---|---|
| | | 0.1 × D mm | 0.2 × D mm | 0.4 × D mm | 0.6 × D mm | 0.8 × D mm | D mm |
| 0° | $\sigma^+_{max}$ | 2.76 | 2.80 | 2.87 | 2.64 | 2.57 | |
| | $\sigma^-_{max}/1.45$ | | | | 2.66 | 2.65 | |
| | $\sigma_{e.max}/1.45$ | | | | | 2.58 | |
| 10° | $\sigma^+_{max}$ | 3.02 | 2.86 | 2.84 | 2.72 | 2.65 | 2.62 |
| | $\sigma^-_{max}/1.45$ | | | | | 2.81 | 3.10 |
| | $\sigma_{e.max}/1.45$ | | | | | | 2.65 |
| 20° | $\sigma^+_{max}$ | 2.78 | 2.55 | 2.52 | 2.64 | 2.63 | 2.51 |
| | $\sigma^-_{max}/1.45$ | | | | | 3.14 | 3.75 |
| | $\sigma_{e.max}/1.45$ | | | | | | 2.90 |
| 30° | $\sigma^+_{max}$ | 2.46 | 2.25 | 2.15 | 2.21 | 2.29 | 2.37 |
| | $\sigma^-_{max}/1.45$ | | | | 2.22 | 2.72 | 3.29 |
| | $\sigma_{e.max}/1.45$ | | | | | | 2.57 |
| 40° | $\sigma^+_{max}$ | 2.17 | 1.98 | 1.83 | 1.81 | 1.83 | 1.89 |
| | $\sigma^-_{max}/1.45$ | 2.19 | 2.19 | 2.25 | 2.31 | 2.40 | 2.68 |
| | $\sigma_{e.max}/1.45$ | 2.25 | | | 1.91 | 2.00 | 2.14 |
| 50° | $\sigma^+_{max}$ | 2.15 | 1.88 | 1.67 | 1.59 | 1.56 | 1.55 |
| | $\sigma^-_{max}/1.45$ | 2.70 | 2.53 | 2.52 | 2.55 | 2.59 | 2.66 |
| | $\sigma_{e.max}/1.45$ | 2.51 | 2.27 | 2.03 | 1.95 | 2.01 | 2.08 |
| 60° | $\sigma^+_{max}$ | 2.49 | 2.22 | 1.89 | 1.71 | 1.61 | 1.55 |
| | $\sigma^-_{max}/1.45$ | 3.68 | 3.53 | 3.31 | 3.13 | 3.30 | 3.48 |
| | $\sigma^-_{max}/2.61$ | | | | 1.74 | 1.83 | 1.93 |
| | $\sigma_{e.max}/1.45$ | 3.10 | 2.90 | 2.66 | 2.46 | 2.43 | 2.56 |

TABLE 2

Thread depth = 0.2 mm. No straight part at the bottom of the thread. The value of $\sigma^+_{max}$ for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given. The value of the top radius expressed as a coefficient multiplied with the thread depth (D).

| Flank angle | | Top radius | | | | | |
|---|---|---|---|---|---|---|---|
| | | 0.1 × D mm | 0.2 × D mm | 0.4 × D mm | 0.6 × D mm | 0.8 × D mm | D mm |
| 0° | $\sigma^+_{max}$ | 2.65 | 2.59 | 2.44 | 2.24 | 2.19 | |
| | $\sigma^-_{max}/1.45$ | | | | 2.30 | 2.36 | |
| | $\sigma_{e.max}/1.45$ | | | | | 2.28 | |
| 10° | $\sigma^+_{max}$ | 2.96 | 2.62 | 2.39 | 2.25 | 2.08 | 2.12 |
| | $\sigma^-_{max}/1.45$ | | | | | 2.27 | 2.40 |
| | $\sigma_{e.max}/1.45$ | | | | | 2.17 | 2.32 |
| 20° | $\sigma^+_{max}$ | 2.80 | 2.51 | 2.34 | 2.23 | 2.06 | 1.99 |
| | $\sigma^-_{max}/1.45$ | | | | | 2.63 | 3.11 |
| | $\sigma_{e.max}/1.45$ | | | | | 2.10 | 2.46 |
| 30° | $\sigma^+_{max}$ | 2.51 | 2.28 | 2.12 | 2.06 | 2.01 | 1.98 |
| | $\sigma^-_{max}/1.45$ | | | | | 2.37 | 2.84 |
| | $\sigma_{e.max}/1.45$ | | | | | | 2.26 |
| 40° | $\sigma^+_{max}$ | 2.23 | 2.02 | 1.86 | 1.81 | 1.78 | 1.78 |
| | $\sigma^-_{max}/1.45$ | 2.63 | 2.32 | 2.09 | 2.09 | 2.12 | 2.41 |
| | $\sigma_{e.max}/1.45$ | 2.37 | | | | | 1.93 |
| 50° | $\sigma^+_{max}$ | 2.24 | 1.95 | 1.72 | 1.63 | 1.59 | 1.57 |
| | $\sigma^-_{max}/1.45$ | 3.14 | 3.18 | 2.52 | 2.38 | 2.39 | 2.42 |
| | $\sigma_{e.max}/1.45$ | 2.68 | 2.37 | 2.01 | 1.96 | 1.90 | 1.92 |
| 60° | $\sigma^+_{max}$ | 2.58 | 2.30 | 1.94 | 1.76 | 1.66 | 1.59 |
| | $\sigma^-_{max}/1.45$ | 4.09 | 3.83 | 3.50 | 3.10 | 3.41 | 3.60 |
| | $\sigma^-_{max}/2.61$ | | | 1.95 | 1.82 | 1.90 | 2.00 |
| | $\sigma_{e.max}/1.45$ | 3.38 | 3.10 | 2.69 | 2.43 | 2.54 | 2.67 |

TABLE 3

Thread depth = 0.3 mm. No straight part at the bottom of the thread. The value of $\sigma^+_{max}$ for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given. The value of the top radius expressed as a coefficient multiplied with the thread depth (D).

| Flank angle | | Top radius | | | | | |
|---|---|---|---|---|---|---|---|
| | | 0.1 × D mm | 0.2 × D mm | 0.4 × D mm | 0.6 × D mm | 0.8 × D mm | D mm |
| 0° | $\sigma^+_{max}$ | 2.54 | 2.42 | 2.11 | 2.04 | 1.99 | |
| | $\sigma^-_{max}/1.45$ | | | | 2.17 | 2.21 | |
| | $\sigma_{e.max}/1.45$ | | | | 2.14 | 2.19 | |
| 10° | $\sigma^+_{max}$ | 2.82 | 2.43 | 2.13 | 1.92 | 1.88 | 1.93 |
| | $\sigma^-_{max}/1.45$ | | | | | 2.12 | 2.23 |
| | $\sigma_{e.max}/1.45$ | | | | | 2.08 | 2.20 |
| 20° | $\sigma^+_{max}$ | 2.78 | 2.42 | 2.12 | 1.95 | 1.80 | 1.69 |
| | $\sigma^-_{max}/1.45$ | | | | 1.98 | 2.44 | 2.88 |
| | $\sigma_{e.max}/1.45$ | | | | | 1.97 | 2.30 |
| 30° | $\sigma^+_{max}$ | 2.54 | 2.27 | 2.04 | 1.91 | 1.78 | 1.71 |
| | $\sigma^-_{max}/1.45$ | | | | | 2.23 | 2.26 |
| | $\sigma_{e.max}/1.45$ | | | | | 1.88 | 2.16 |
| 40° | $\sigma^+_{max}$ | 2.29 | 2.04 | 1.86 | 1.77 | 1.70 | 1.65 |
| | $\sigma^-_{max}/1.45$ | 2.73 | 2.37 | 1.97 | 1.97 | 2.01 | 2.28 |
| | $\sigma_{e.max}/1.45$ | 2.39 | | | | | 1.86 |
| 50° | $\sigma^+_{max}$ | 2.30 | 1.99 | 1.75 | 1.65 | 1.59 | 1.55 |
| | $\sigma^-_{max}/1.45$ | 3.25 | 2.94 | 2.54 | 2.29 | 2.28 | 2.34 |
| | $\sigma_{e.max}/1.45$ | 2.77 | 2.37 | 2.01 | 1.92 | 1.83 | 1.85 |
| 60° | $\sigma^+_{max}$ | 2.64 | 2.34 | 1.98 | 1.80 | 1.69 | 1.62 |
| | $\sigma^-_{max}/1.45$ | 4.18 | 3.90 | 3.54 | 3.38 | 3.57 | 3.75 |
| | $\sigma^-_{max}/2.61$ | | | | 1.88 | 1.98 | 2.08 |
| | $\sigma_{e.max}/1.45$ | 3.48 | 3.16 | 2.68 | 2.56 | 2.68 | 2.81 |

TABLE 4

Thread depth = 0.4 mm. No straight part at the bottom of the thread. The value of $\sigma^+_{max}$ for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given. The value of the top radius expressed as a coefficient multiplied with the thread depth (D).

| Flank angle | | Top radius | | | | | |
|---|---|---|---|---|---|---|---|
| | | 0.1 × D mm | 0.2 × D mm | 0.4 × D mm | 0.6 × D mm | 0.8 × D mm | D mm |
| 0° | $\sigma^+_{max}$ | 2.41 | 2.22 | 1.96 | 1.91 | 1.87 | |
| | $\sigma^-_{max}/1.45$ | | | | 2.07 | 2.11 | |
| | $\sigma_{e.max}/1.45$ | | | 1.98 | 2.08 | 2.14 | |
| 10° | $\sigma^+_{max}$ | 2.72 | 2.26 | 1.93 | 1.75 | 1.77 | 1.81 |
| | $\sigma^-_{max}/1.45$ | | | | 1.82 | 2.01 | 2.14 |
| | $\sigma_{e.max}/1.45$ | | | 1.87 | 2.04 | 2.16 | |
| 20° | $\sigma^+_{max}$ | 2.76 | 2.34 | 1.96 | 1.75 | 1.62 | 1.58 |
| | $\sigma^-_{max}/1.45$ | | | | 1.90 | 2.35 | 2.77 |
| | $\sigma_{e.max}/1.45$ | | | | 1.92 | 2.23 | |
| 30° | $\sigma^+_{max}$ | 2.55 | 2.26 | 1.96 | 1.75 | 1.63 | 1.52 |
| | $\sigma^-_{max}/1.45$ | | | | 1.78 | 2.15 | 2.58 |
| | $\sigma_{e.max}/1.45$ | | | | | 1.84 | 2.12 |
| 40° | $\sigma^+_{max}$ | 2.33 | 2.06 | 1.85 | 1.72 | 1.60 | 1.52 |
| | $\sigma^-_{max}/1.45$ | 2.77 | 2.38 | 1.94 | 1.90 | 1.95 | 2.22 |
| | $\sigma_{e.max}/1.45$ | 2.39 | | | | 1.66 | 1.84 |
| 50° | $\sigma^+_{max}$ | 2.35 | 2.03 | 1.76 | 1.65 | 1.58 | 1.51 |
| | $\sigma^-_{max}/1.45$ | 3.29 | 2.95 | 2.54 | 2.27 | 2.23 | 2.43 |
| | $\sigma_{e.max}/1.45$ | 2.81 | 2.35 | 2.01 | 1.90 | 1.81 | 1.94 |
| 60° | $\sigma^+_{max}$ | 2.68 | 2.38 | 2.01 | 1.82 | 1.70 | 1.63 |
| | $\sigma^-_{max}/1.45$ | 4.21 | 3.92 | 3.53 | 3.54 | 3.74 | 3.93 |
| | $\sigma^-_{max}/2.61$ | | | | 1.97 | 2.08 | 2.18 |
| | $\sigma_{e.max}/1.45$ | 3.59 | 3.20 | 2.68 | 2.70 | 2.83 | 2.97 |
| | $\sigma_{e.max}/2.61$ | | | | | | 1.65 |

TABLE 5

Thread depth = 0.1 mm. The lengths of the straight part of S at the bottom of the thread which minimize the maximum compressive stress, the maximum tensile stress and the maximum von Mieses stress respectively. This length is expressed as a coefficient c which is to be multiplied with the length of the curved part (L) of the thread (FIG. 1). The table lists the values of this coefficient.

| Flank angle | Min. Stress | Top radius | | | | | |
|---|---|---|---|---|---|---|---|
| | | 0.1 × D mm | 0.2 × D mm | 0.4 × D mm | 0.6 × D mm | 0.8 × D mm | 1 × D mm |
| 0° | $\sigma^-_{max}$ | 0 | 0.4 | 0.2 | 0.2 | 0.2 | — |
| | $\sigma^+_{max}$ | 0 | 0.4 | 0.4 | 0.8 | 0.8 | — |
| | $\sigma_{e.max}$ | 0 | 0.4 | 0.4 | 0.4 | 0.2 | — |
| 10° | $\sigma^-_{max}$ | 0 | 0 | 0 | 0 | 0 | 0 |
| | $\sigma^+_{max}$ | 0 | 0 | 0.8 | 0.8 | 0.8 | 0.8 |
| | $\sigma_{e.max}$ | 0 | 0 | 0.4 | 0.4 | 0.2 | 0 |
| 20° | $\sigma^-_{max}$ | 0 | 0 | 0 | 0.2 | 0.2 | 0 |
| | $\sigma^+_{max}$ | 0 | 0 | 0.4 | 0.8 | 0.8 | 0.4 |
| | $\sigma_{e.max}$ | 0 | 0 | 0.4 | 0.4 | 0.4 | 0.2 |
| 30° | $\sigma^-_{max}$ | 0 | 0 | 0 | 0 | 0 | 0 |
| | $\sigma^+_{max}$ | 0 | 0 | 0 | 0.4 | 0.4 | 0.4 |
| | $\sigma_{e.max}$ | 0 | 0 | 0 | 0.2 | 0.2 | 0.2 |
| 40° | $\sigma^-_{max}$ | 0 | 0 | 0 | 0 | 0 | 0 |
| | $\sigma^+_{max}$ | 0 | 0 | 0 | 0.2 | 0.2 | 0.2 |
| | $\sigma\sigma_{e.max}$ | 0 | 0 | 0 | 0 | 0 | 0.2 |
| 50° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |
| 60° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |

TABLE 6

Thread depth = 0.2 mm. The lengths of the straight part of S at the bottom of the thread which minimize the maximum compressive stress, the maximum tensile stress and the maximum von Mieses stress respectively. This length is expressed as a coefficient c which is to be multiplied with the length of the curved part (L) of the thread (FIG. 1). The table lists the values of this coefficient.

| Flank angle | Min. Stress | Top radius | | | | | |
|---|---|---|---|---|---|---|---|
| | | 0.1 × D mm | 0.2 × D mm | 0.4 × D mm | 0.6 × D mm | 0.8 × D mm | 1 × D mm |
| 0° | $\sigma^-_{max}$ | 0 | 0.4 | 0.4 | 0.2 | 0 | — |
| | $\sigma^+_{max}$ | 0 | 0.4 | 0.4 | 0.8 | 0.8 | — |
| | $\sigma_{e.max}$ | 0 | 0.4 | 0.4 | 0.8 | 0.2 | — |
| 10° | $\sigma^-_{max}$ | 0 | 0 | 0.2 | 0 | 0 | 0 |
| | $\sigma^+_{max}$ | 0 | 0.2 | 0.4 | 0.8 | 0.8 | 0.8 |
| | $\sigma_{e.max}$ | 0 | 0 | 0.4 | 0.4 | 0.2 | 0 |
| 20° | $\sigma^-_{max}$ | 0 | 0 | 0 | 0 | 0 | 0 |
| | $\sigma^+_{max}$ | 0 | 0 | 0.4 | 0.8 | 0.4 | 0.8 |
| | $\sigma_{e.max}$ | 0 | 0 | 0.2 | 0.4 | 0.4 | 0.2 |
| 30° | $\sigma^-_{max}$ | 0 | 0 | 0 | 0 | 0 | 0 |
| | $\sigma^+_{max}$ | 0 | 0 | 0 | 0.4 | 0.4 | 0.4 |
| | $\sigma_{e.max}$ | 0 | 0 | 0 | 0.2 | 0.2 | 0.2 |
| 40° | $\sigma^-_{max}$ | 0 | 0 | 0 | 0 | 0 | 0 |
| | $\sigma^+_{max}$ | 0 | 0 | 0 | 0 | 0.2 | 0.2 |
| | $\sigma_{e.max}$ | 0 | 0 | 0 | 0 | 0 | 0.2 |
| 50° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |
| 60° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |

TABLE 7

Thread depth = 0.3 mm. The lengths of the straight part of S at the bottom of the thread which minimize the maximum compressive stress, the maximum tensile stress and the maximum von Mieses stress respectively. This length is expressed as a coefficient c which is to be multiplied with the length of the curved part (L) of the thread (FIG. 1). The table lists the values of this coefficient.

| Flank angle | Min. Stress | Top radius | | | | | |
|---|---|---|---|---|---|---|---|
| | | 0.1 × D mm | 0.2 × D mm | 0.4 × D mm | 0.6 × D mm | 0.8 × D mm | 1 × D mm |
| 0° | $\sigma^-_{max}$ | 0 | 0.4 | 0.4 | 0.2 | 0 | — |
| | $\sigma^+_{max}$ | 0.2 | 0.4 | 0.8 | 0.8 | 0.8 | — |
| | $\sigma_{e.max}$ | 0 | 0.4 | 0.4 | 0.8 | 0.2 | — |
| 10° | $\sigma^-_{max}$ | 0 | 0 | 0.2 | 0 | 0 | 0 |
| | $\sigma^+_{max}$ | 0 | 0 | 0.4 | 0.8 | 0.8 | 0.4 |
| | $\sigma_{e.max}$ | 0 | 0 | 0.4 | 0.4 | 0.2 | 0 |
| 20° | $\sigma^-_{max}$ | 0 | 0 | 0 | 0 | 0 | 0 |
| | $\sigma^+_{max}$ | 0 | 0 | 0.2 | 0.4 | 0.4 | 0.4 |
| | $\sigma_{e.max}$ | 0 | 0 | 0.2 | 0.4 | 0.2 | 0.2 |
| 30° | $\sigma^-_{max}$ | 0 | 0 | 0 | 0 | 0 | 0 |
| | $\sigma^+_{max}$ | 0 | 0 | 0 | 0.4 | 0.2 | 0.4 |
| | $\sigma_{e.max}$ | 0 | 0 | 0 | 0.2 | 0.2 | 0.2 |
| 40° | $\sigma^-_{max}$ | 0 | 0 | 0 | 0 | 0 | 0 |
| | $\sigma^+_{max}$ | 0 | 0 | 0 | 0 | 0 | 0.2 |
| | $\sigma_{e.max}$ | 0 | 0 | 0 | 0 | 0 | 0 |
| 50° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |
| 60° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |

TABLE 8

Thread depth = 0.4 mm. The lengths of the straight part of S at the bottom of the thread which minimize the maximum compressive stress, the maximum tensile stress and the maximum von Mieses stress respectively. This length is expressed as a coefficient c which is to be multiplied with the length of the curved part (L) of the thread (FIG. 1). The table lists the values of this coefficient.

| Flank angle | Min. Stress | Top radius | | | | | |
|---|---|---|---|---|---|---|---|
| | | $0.1 \times D$ mm | $0.2 \times D$ mm | $0.4 \times D$ mm | $0.6 \times D$ mm | $0.8 \times D$ mm | $1 \times D$ mm |
| 0° | $\sigma^-_{max}$ | 0 | 0.4 | 0.4 | 0.2 | 0 | — |
| | $\sigma^+_{max}$ | 0 | 0.4 | 0.4 | 0.8 | 0.8 | — |
| | $\sigma_{e.max}$ | 0 | 0.2 | 0.4 | 0.8 | 0.2 | — |
| 10° | $\sigma^-_{max}$ | 0 | 0 | 0.2 | 0 | 0 | 0 |
| | $\sigma^+_{max}$ | 0 | 0 | 0.2 | 0.4 | 0.8 | 0.8 |
| | $\sigma_{e.max}$ | 0 | 0 | 0.2 | 0.4 | 0.2 | 0 |
| 20° | $\sigma^-_{max}$ | 0 | 0 | 0 | 0 | 0 | 0 |
| | $\sigma^+_{max}$ | 0 | 0 | 0 | 0.2 | 0.4 | 0.4 |
| | $\sigma_{e.max}$ | 0 | 0 | 0 | 0.2 | 0.2 | 0.2 |
| 30° | $\sigma^-_{max}$ | 0 | 0 | 0 | 0 | 0 | 0 |
| | $\sigma^+_{max}$ | 0 | 0 | 0 | 0 | 0.2 | 0.2 |
| | $\sigma_{e.max}$ | 0 | 0 | 0 | 0.2 | 0.2 | 0 |
| 40° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |
| 50° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |
| 60° | $\sigma^-_{max}$ | 0 | 0 | 0 | 0 | 0 | 0 |
| | $\sigma^+_{max}$ | 0 | 0 | 0 | 0 | 0 | 0 |
| | $\sigma_{e.max}$ | 0 | 0 | 0 | 0 | 0 | 0 |

TABLE 9

Thread depth = 0.1 mm. The lowest of the values of $\sigma^+_{max}$ for different lengths of the straight part at the bottom of the thread (c = 0, 0.2, 0.4, 0.8, 1.6) for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given (for the combination of parameters which minimized $\sigma^+_{max}$). The value of the top radius expressed as a coefficient multiplied with the thread depth (D).

| Flank angle | | Top radius | | | | | |
|---|---|---|---|---|---|---|---|
| | | $0.1 \times D$ mm | $0.2 \times D$ mm | $0.4 \times D$ mm | $0.6 \times D$ mm | $0.8 \times D$ mm | D mm |
| 0° | $\sigma^+_{max}$ | 2.76 | 2.48 | 2.33 | 2.13 | 2.02 | |
| | $\sigma^-_{max}/1.45$ | | | | 2.92 | 6.17 | |
| | $\sigma^-_{max}/2.61$ | | | | | 3.42 | |
| | $\sigma_{e.max}/1.45$ | | | | | 3.48 | |
| 10° | $\sigma^+_{max}$ | 3.02 | 2.86 | 2.54 | 2.32 | 2.11 | 2.05 |
| | $\sigma^-_{max}/1.45$ | | | | 3.05 | 4.59 | 8.71 |
| | $\sigma^-_{max}/2.61$ | | | | | 2.55 | 4.84 |
| | $\sigma_{e.max}/1.45$ | | | | | 2.66 | 5.24 |
| | $\sigma_{e.max}/2.61$ | | | | | | 2.91 |
| 20° | $\sigma^+_{max}$ | 2.78 | 2.55 | 2.46 | 2.27 | 2.18 | 2.06 |
| | $\sigma^-_{max}/1.45$ | | | | 3.02 | 4.04 | 4.23 |
| | $\sigma^-_{max}/2.61$ | | | | | 2.25 | 2.35 |
| | $\sigma_{e.max}/1.45$ | | | | | 2.44 | 2.64 |
| 30° | $\sigma^+_{max}$ | 2.46 | 2.25 | 2.15 | 2.05 | 2.01 | 1.97 |
| | $\sigma^-_{max}/1.45$ | | | | 2.46 | 2.95 | 3.58 |
| | $\sigma^-_{max}/2.61$ | | | | | | 1.99 |
| | $\sigma_{e.max}/1.45$ | | | | | 2.10 | 2.34 |
| 40° | $\sigma^+_{max}$ | 2.17 | 1.98 | 1.83 | 1.80 | 1.76 | 1.75 |
| | $\sigma^-_{max}/1.45$ | 2.19 | 2.19 | 2.25 | 2.52 | 2.58 | 2.87 |
| | $\sigma_{e.max}/1.45$ | 2.24 | | | 1.99 | 2.02 | 2.11 |
| 50° | $\sigma^+_{max}$ | 2.15 | 1.88 | 1.67 | 1.59 | 1.56 | 1.55 |
| | $\sigma^-_{max}/1.45$ | 2.70 | 2.53 | 2.52 | 2.55 | 2.60 | 2.66 |
| | $\sigma_{e.max}/1.45$ | 2.51 | 2.27 | 2.03 | 1.95 | 2.02 | 2.08 |
| 60° | $\sigma^+_{max}$ | 2.49 | 2.22 | 1.89 | 1.71 | 1.61 | 1.55 |
| | $\sigma^-_{max}/1.45$ | 3.68 | 3.53 | 3.31 | 3.13 | 3.30 | 3.48 |
| | $\sigma^-_{max}/2.61$ | | | | 1.74 | 1.83 | 1.93 |
| | $\sigma_{e.max}/1.45$ | 3.11 | 2.91 | 2.66 | 2.46 | 2.43 | 2.56 |

TABLE 10

Thread depth = 0.2 mm. The lowest of the values of $\sigma^+_{max}$ for different lengths of the straight part at the bottom of the thread (c = 0, 0.2, 0.4, 0.8, 1.6) for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given (for the combination of parameters which minimized $\sigma^+_{max}$). The value of the top radius expressed as a coefficient multiplied with the thread depth (D).

| Flank angle | | 0.1 × D mm | 0.2 × D mm | 0.4 × D mm | 0.6 × D mm | 0.8 × D mm | D mm |
|---|---|---|---|---|---|---|---|
| 0° | $\sigma^+_{max}$ | 2.65 | 2.35 | 2.11 | 1.89 | 1.74 | |
| | $\sigma^-_{max}/1.45$ | | | | 2.62 | 5.59 | |
| | $\sigma^-_{max}/2.61$ | | | | | 3.10 | |
| | $\sigma_{e.max}/1.45$ | | | | | 3.18 | |
| | $\sigma_{e.max}/2.61$ | | | | | 1.77 | |
| 10° | $\sigma^+_{max}$ | 2.96 | 2.61 | 2.25 | 1.97 | 1.85 | 1.71 |
| | $\sigma^-_{max}/1.45$ | | | | 2.72 | 4.12 | 7.86 |
| | $\sigma^-_{max}/2.61$ | | | | | 2.29 | 4.37 |
| | $\sigma_{e.max}/1.45$ | | | | | 2.44 | 4.75 |
| | $\sigma_{e.max}/2.61$ | | | | | | 2.64 |
| 20° | $\sigma^+_{max}$ | 2.80 | 2.51 | 2.28 | 2.80 | 1.93 | 1.78 |
| | $\sigma^-_{max}/1.45$ | | | | 2.23 | 2.83 | 3.72 |
| | $\sigma^-_{max}/2.61$ | | | | | | 2.07 |
| | $\sigma_{e.max}/1.45$ | | | | | | 2.39 |
| 30° | $\sigma^+_{max}$ | 2.51 | 2.28 | 2.12 | 2.01 | 1.88 | 1.79 |
| | $\sigma^-_{max}/1.45$ | | | | 2.20 | 2.63 | 3.19 |
| | $\sigma_{e.max}/1.45$ | | | | | 1.89 | 2.12 |
| 40° | $\sigma^+_{max}$ | 2.24 | 2.02 | 1.86 | 1.81 | 1.77 | 1.71 |
| | $\sigma^-_{max}/1.45$ | 2.63 | 2.32 | 2.08 | 2.09 | 2.30 | 2.56 |
| | $\sigma_{e.max}/1.45$ | 2.37 | | | | 1.81 | 1.92 |
| 50° | $\sigma^+_{max}$ | 2.24 | 1.95 | 1.72 | 1.63 | 1.59 | 1.57 |
| | $\sigma^-_{max}/1.45$ | 3.14 | 2.87 | 2.52 | 2.38 | 2.39 | 2.42 |
| | $\sigma_{e.max}/1.45$ | 2.67 | 2.37 | 2.01 | 1.96 | 1.90 | 1.92 |
| 60° | $\sigma^+_{max}$ | 2.58 | 2.30 | 1.94 | 1.76 | 1.66 | 1.59 |
| | $\sigma^-_{max}/1.45$ | 4.09 | 3.83 | 3.50 | 3.28 | 3.41 | 3.60 |
| | $\sigma^-_{max}/2.61$ | 2.27 | 2.13 | 1.95 | 1.82 | 1.90 | 2.00 |
| | $\sigma_{e.max}/1.45$ | 3.38 | 3.10 | 2.69 | 2.43 | 2.54 | 2.67 |

TABLE 11

Thread depth = 0.3 mm. The lowest of the values of $\sigma^+_{max}$ for different lengths of the straight part at the bottom of the thread (c = 0, 0.2, 0.4, 0.8, 1.6) for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given (for the combination of parameters which minimized $\sigma^+_{max}$). The value of the top radius expressed as a coefficient multiplied with the thread depth (D).

| Flank angle | | 0.1 × D mm | 0.2 × D mm | 0.4 × D mm | 0.6 × D mm | 0.8 × D mm | D mm |
|---|---|---|---|---|---|---|---|
| 0° | $\sigma^+_{max}$ | 2.48 | 2.20 | 1.93 | 1.72 | 1.59 | |
| | $\sigma^-_{max}/1.45$ | | | | 2.50 | 5.38 | |
| | $\sigma^-_{max}/2.61$ | | | | | 2.98 | |
| | $\sigma_{e.max}/1.45$ | | | | | 3.07 | |
| | $\sigma_{e.max}/2.61$ | | | | | 1.70 | |
| 10° | $\sigma^+_{max}$ | 2.82 | 2.43 | 2.04 | 1.81 | 1.63 | 1.54 |
| | $\sigma^-_{max}/1.45$ | | | | 2.12 | 3.97 | 7.62 |
| | $\sigma^-_{max}/2.61$ | | | | | 2.20 | 4.23 |
| | $\sigma_{e.max}/1.45$ | | | | | 2.38 | 4.62 |
| | $\sigma_{e.max}/2.61$ | | | | | | 2.57 |
| 20° | $\sigma^+_{max}$ | 2.77 | 2.42 | 2.11 | 1.88 | 1.68 | 1.57 |
| | $\sigma^-_{max}/1.45$ | | | | 2.11 | 2.70 | 2.55 |
| | $\sigma^-_{max}/2.61$ | | | | | 1.97 | |
| | $\sigma_{e.max}/1.45$ | | | | | 1.88 | 2.32 |
| 30° | $\sigma^+_{max}$ | 2.53 | 2.27 | 2.04 | 1.91 | 1.72 | 1.60 |
| | $\sigma^-_{max}/1.45$ | | | | | 2.30 | 3.05 |
| | $\sigma^-_{max}/2.61$ | | | | | | 1.69 |
| | $\sigma_{e.max}/1.45$ | | | | | 1.79 | 2.08 |
| 40° | $\sigma^+_{max}$ | 2.29 | 2.04 | 1.86 | 1.77 | 1.70 | 1.63 |
| | $\sigma^-_{max}/1.45$ | 2.73 | 2.37 | 1.97 | 1.97 | 2.01 | 2.61 |
| | $\sigma_{e.max}/1.45$ | 2.39 | | | | | 1.88 |
| 50° | $\sigma^+_{max}$ | 2.30 | 2.00 | 1.75 | 1.65 | 1.59 | 1.55 |
| | $\sigma^-_{max}/1.45$ | 3.25 | 2.94 | 2.54 | 2.29 | 2.28 | 2.34 |
| | $\sigma_{e.max}/1.45$ | 2.77 | 2.36 | 2.01 | 1.92 | 1.83 | 1.85 |
| 60° | $\sigma^+_{max}$ | 2.64 | 2.34 | 1.98 | 1.80 | 1.69 | 1.62 |
| | $\sigma^-_{max}/1.45$ | 4.18 | 3.90 | 3.54 | 3.38 | 3.56 | 3.75 |
| | $\sigma^-_{max}/2.61$ | | | | 1.88 | 1.98 | 2.08 |
| | $\sigma_{e.max}/1.45$ | 3.48 | 3.16 | 2.68 | 2.56 | 2.68 | 2.81 |

TABLE 12

Thread depth = 0.4 mm. The lowest of the values of $\sigma^+_{max}$ for different lengths of the straight part at the bottom of the thread (c = 0, 0.2, 0.4, 0.8, 1.6) for different combinations of flank angle and top radius as a result of a standard load per unit length of the implant segment. In the cases when $\sigma^-_{max}/1.45$, $\sigma^-_{max}/2.61$, $\sigma_{e.max}/1.45$ or $\sigma_{e.max}/2.61$ exceed $\sigma^+_{max}$ these values are also given (for the combination of parameters which minimized $\sigma^+_{max}$). The value of the top radius expressed as a coefficient multiplied with the thread depth (D).

| Flank angle | | Top radius | | | | | |
|---|---|---|---|---|---|---|---|
| | | 0.1 × D mm | 0.2 × D mm | 0.4 × D mm | 0.6 × D mm | 0.8 × D mm | D mm |
| 0° | $\sigma^+_{max}$ | 2.41 | 2.08 | 1.79 | 1.65 | 1.53 | |
| | $\sigma^-_{max}/1.45$ | | | | 2.46 | 5.31 | |
| | $\sigma^-_{max}/2.61$ | | | | | 2.95 | |
| | $\sigma_{e.max}/1.45$ | | | | 1.75 | 3.03 | |
| | $\sigma_{e.max}/2.61$ | | | | | 1.69 | |
| 10° | $\sigma^+_{max}$ | 2.72 | 2.26 | 1.88 | 1.67 | 1.52 | 1.43 |
| | $\sigma^-_{max}/1.45$ | | | | 2.06 | 3.92 | 4.98 |
| | $\sigma^-_{max}/2.61$ | | | | | 2.18 | 2.77 |
| | $\sigma_{e.max}/1.45$ | | | | | 2.39 | 4.59 |
| | $\sigma_{e.max}/2.61$ | | | | | | 2.55 |
| 20° | $\sigma^+_{max}$ | 2.76 | 2.34 | 1.96 | 1.72 | 1.55 | 1.42 |
| | $\sigma^-_{max}/1.45$ | | | | 1.94 | 2.64 | 3.49 |
| | $\sigma^-_{max}/2.61$ | | | | | | 1.94 |
| | $\sigma_{e.max}/1.45$ | | | | | 1.87 | 2.32 |
| 30° | $\sigma^+_{max}$ | 2.55 | 2.26 | 1.96 | 1.75 | 1.59 | 1.48 |
| | $\sigma^-_{max}/1.45$ | | | | 1.78 | 2.24 | 2.70 |
| | $\sigma^-_{max}/2.61$ | | | | | | 1.50 |
| | $\sigma_{e.max}/1.45$ | | | | | 1.79 | 1.99 |
| 40° | $\sigma^+_{max}$ | 2.33 | 2.06 | 1.85 | 1.72 | 1.60 | 1.52 |
| | $\sigma^-_{max}/1.45$ | 2.76 | 2.38 | 1.94 | 1.90 | 1.95 | 2.22 |
| | $\sigma_{e.max}/1.45$ | 2.39 | | | | 1.66 | 1.84 |
| 50° | $\sigma^+_{max}$ | 2.34 | 2.03 | 1.76 | 1.65 | 1.58 | 1.51 |
| | $\sigma^-_{max}/1.45$ | 3.29 | 2.95 | 2.54 | 2.27 | 2.23 | 2.43 |
| | $\sigma_{e.max}/1.45$ | 2.81 | 2.35 | 2.01 | 1.90 | 1.81 | 1.94 |
| 60° | $\sigma^+_{max}$ | 2.68 | 2.38 | 2.01 | 1.82 | 1.70 | 1.63 |
| | $\sigma^-_{max}/1.45$ | 4.21 | 3.92 | 3.53 | 3.54 | 3.74 | 3.93 |
| | $\sigma^-_{max}/2.61$ | | | | 1.97 | 2.08 | 2.18 |
| | $\sigma_{e.max}/1.45$ | 3.59 | 3.20 | 2.69 | 2.70 | 2.83 | 2.97 |
| | $\sigma_{e.max}/2.61$ | | | | | | 1.65 |

The radius R has been constant and has been real in the above examples.

In a preferred embodiment, illustrated in FIG. 7, the top radius R at the apex is imaginary and defines a the transition point P1 between the straight flank and the curved apex, a first tangent through P1 being directed along said flank, as well as a crest point P2 on the apex in which a second tangent to the curved part is parallel to the longitudinal direction of the implant. In this embodiment the curved apex has the shape of curved part originating in said points P1 and P2 and has tangents in said points coinciding with said first and second tangents, and has a radius of curvature R1. The radius R1 may for instance increase from a value $R_{min}$ to a value $R_{max}$ or may increase from a value $R_{min}$ to a value $R_{max}$, then decreasing to a value $R_{min}$.

$R_{min}$ should preferably be greater than 0.01 mm and the relationship $R_{max}/R_{min}$ preferably should be greater than 3.

One special case of this embodiment is of course that said radius of curvature R1 is constant and equal to said imaginary radius R, the apex thus having a part circular shape with the radius R.

The following calculations illustrate the effect of the variable radius of curvature.

Uniform top radius=0.04 mm
Flank angle: 40°
Thread depth: 0.1 mm
Bottom radius: 0.01 mm
Maximum tensile stress: 1.784 Mpa
Variable radius of curvature of the thread top-small continuous variations:
Flank angle: 40°
Thread depth: 0,1 mm
Top radius: $R_{min}$=0,025 mm, $R_{max}$=0.055 mm
Bottom radius: 0.01 mm
Maximum tensile stress: 1.750 Mpa
Variable radius of curvature of the thread top—bigger continuous variations:
Flank angle: 40°
Thread depth: 0,1 mm
Top radius: $R_{min}$=0.0010 mm, $R_{max}$=0.069 mm
Bottom radius: 0.01 mm
Maximum tensile stress: 1.721 Mpa As can be seen in the above, there is some improvement with a variable radius of curvature.

The invention of course can be varied in many ways within the scope of the appended claims. It should for instance be noted that the two flank angles of the thread or roughness not necessarily have to be identical even if this is a preferred embodiment. In some applications the angles may be different although both are within the ranges specified, in another applications it may be sufficient that the flank being the most heavily loaded has a flank angle within the ranges specified. The same is valid for the top radius which in similarity may have different values on the respective sides of the thread, both values or only one value being within the ranges specified.

I claim:

1. An implant having a shaft which has a longitudinal axis, is adapted in use to be embedded in bone tissue and has an outer surface on which is provided a circumferentially-oriented macroroughness, wherein the circumferentially-oriented macroroughness is formed by a series of circumferentially-oriented peaks which are axially spaced-apart by grooves, wherein each circumferentially-oriented peak has first and second flanks and a curved apex which connects the first and second flanks, wherein the first and second flanks of each circumferentially-oriented peak have a bottom radius (r) at the respective adjacent groove and a straight part which extends from the bottom radius to a transition point (P1) between the flank and the curved apex at which a first tangent extends along the straight part, wherein each curved apex has a crest point (P2) at which a second tangent extends parallel to the longitudinal axis of the shaft, wherein the circumferentially-oriented macroroughness has a predetermined height (D), as measured from the crest points on the curved apexes to the grooves, wherein the straight part of each first and second flank is oriented at an angle (v) to a plane which is perpendicular to the longitudinal axis of the shaft, which angle is in the range 10°≦v≦55°, wherein the curved apex of each peak comprises a curved part of a predetermined radius of curvature connecting the transition point on a predetermined one of the associated first and second flanks and the crest point, wherein the curved apex of each peak has an imaginary top radius (R) which connects the transition point on the predetermined associated flank and the crest point, and wherein R>0.4D for the predetermined flanks having $10° \leq v < 35°$ and R>0.2D for the predetermined flanks having $35 \leq v \leq 55°$.

2. The implant of claim 1, wherein the predetermined flanks have $10° \leq v < 35°$, wherein 0.15 mm $\leq D \leq$ 0.25 mm, wherein the grooves have a bottom length (S) in the range $0.5D \leq S \leq 2D$ and wherein $0.5D < R < 0.7D$.

3. The implant of claim 1, wherein the predetermined flanks have $35° \leq v \leq 55°$, wherein 0.05 mm $\leq D \leq$ 0.5 mm and wherein $0.2D < R < D$.

4. The implant of claim 3, wherein 0.05 mm $\leq D \leq$ 0.25 mm.

5. The implant of claim 3, wherein 0.05 mm $\leq D \leq$ 0.15 mm.

6. The implant of claim 3, wherein 0.05 mm $\leq D \leq$ 0.1 mm.

7. The implant of claim 1, wherein the predetermined flanks have $10° \leq v < 35°$, wherein 0.25 mm $\leq D \leq$ 0.5 mm and wherein $0.4D < R < D$.

8. The implant of claim 7, wherein $0.6D < R < D$.

9. The implant of claim 1, wherein the predetermined flanks have $37 \leq v \leq 43°$, wherein 0.03 mm $\leq R \leq$ 0.05 mm, wherein 0.01 mm $\leq r \leq$ 0.025 mm and wherein 0.08 mm $\leq D \leq$ 0.15 mm.

10. The implant of any one of claims 1 to 9, wherein the axial spacing between the crest points of adjacent peaks is smaller than 3D.

11. The implant of any one of claims 1 to 9, wherein the axial spacing between the crest points of adjacent peaks is smaller than 2D.

12. The implant of any one of claims 1 to 6, wherein the predetermined radius of curvature of each curved part is constant and equal to the associated imaginary top radius.

13. The implant of any one of claims 1 to 9, wherein the peaks of the circumferentially-oriented macroroughness are symmetrical.

14. The implant of any one of claims 1 to 9, wherein the curved part of each curved apex is a first curved part connecting the transition point on the associated first flank and the crest point, wherein each curved apex has a second curved part of a predetermined radius of curvature connecting the transition point on the associated second flank and the crest point, wherein each curved apex has an imaginary top radius (W) which connects the transition point on the associated second flank and the crest point and wherein R'>0.4D for the associated second flanks having $10° \leq v < 35°$ and R'<0.2D for the associated second flanks having $35° \geq v \geq 55°$.

15. The implant of any one of claims 1 to 9, wherein the peaks in the series are identical to one another.

16. The implant of claim 1 or any one of claim 3 to 9, wherein the bottom radii of adjacent flanks are contiguous with one another.

17. The implant of any one of claims 1 to 9, wherein r=0.1D.

18. The implant of any one of claims 1 to 9, wherein the circumferentially-oriented macroroughness is a screw thread.

19. The implant of claim 18, wherein the screw thread is one of two or more different screw threads on the shaft of the implant.

20. The implant of any one of claims 1 to 9, wherein a microroughness having a pore size in the range 2–20 $\mu$m is superimposed on the circumferentially-oriented macroroughness.

21. The implant of claim 20, wherein the microroughness has a pore size in the range 2–10 $\mu$m.

22. The implant of any one of claims 1 to 9, wherein the predetermined radius of curvature of each curved part varies between a maximum value and a minimum value.

23. The implant of claim 22, wherein the ratio of the maximum value of the predetermined radius of curvature to the minimum value is greater than 3.

24. The implant of claim 22, wherein the minimum value of the predetermined radius of curvature of each curved part is greater than 0.01 mm.

25. The implant of claim 1, wherein D=0.1 mm.

* * * * *

UNITED STATES PATENT AND TRADEMARK OFFICE
CERTIFICATE OF CORRECTION

PATENT NO. : 6,036,491
DATED : March 14, 2000
INVENTOR(S) : Hansson

It is certified that error appears in the above-identified patent and that said Letters Patent is hereby corrected as shown below:

In the Abstract, delete all appearances of "$\leq$" and insert therefor --$\leq$--.

In the Specification

Column 3,
Lines 4,5,7 and 8, delete all appearances of "$\leq$" and insert therefor --$\leq$--.

Column 5,
Lines 4-6, delete all appearances of "$\leq$" and insert therefor --$\leq$--.

In Claims 1-7,
Columns 18 and 19, delete all appearances of "$\leq$" and insert therefor --$\leq$--.

In Claim 9,
Column 19, delete all appearances of "$\leq$" and insert therefor -- $\leq$ --; at line 25, delete "37" and insert therefor -- 37° --.

UNITED STATES PATENT AND TRADEMARK OFFICE
CERTIFICATE OF CORRECTION

PATENT NO.   : 6,036,491
DATED        : March 14, 2000
INVENTOR(S)  : Hansson

It is certified that error appears in the above-identified patent and that said Letters Patent is hereby corrected as shown below:

In Claim 12,
Column 19, at line 34, delete "claims 1 to 6" and insert therefor
-- claims 1 to 9 --.

In Claim 14,
Column 20, at line 6, delete "(W)" and insert therefor -- (R') --;
at line 9, delete "R'<0.2D" and insert therefor -- R'>0.2D --; and at line
10, delete "35°≥v≥55°" and insert therefor -- 35°≤v ≤55° --.

Signed and Sealed this

Twenty-sixth Day of June, 2001

Attest:

NICHOLAS P. GODICI
Attesting Officer        Acting Director of the United States Patent and Trademark Office

UNITED STATES PATENT AND TRADEMARK OFFICE
CERTIFICATE OF CORRECTION

PATENT NO. : 6,036,491
DATED : March 14, 2000
INVENTOR(S) : Hansson

Page 1 of 1

It is certified that error appears in the above-identified patent and that said Letters Patent is hereby corrected as shown below:

<u>Title page,</u>
ABSTRACT, delete all appearances of "$\leq$" and insert therefor -- $\leqq$ --.

<u>Column 3,</u>
Lines 4, 5, 7 and 8, delete all appearances of "$\leq$" and insert therefor -- $\leqq$ --.

<u>Column 5,</u>
Lines 4-6, delete all appearances of "$\leq$" and insert therefor -- $\leqq$ --.

<u>Columns 18-19, claims 1-7,</u>
Delete all appearances of "$\leq$" and insert therefor -- $\leqq$ --.

<u>Column 19, claim 9,</u>
Delete all appearances of "$\leq$" and insert therefor -- $\leqq$ --.
Line 25, delete "37" and insert therefor -- 37° --.

<u>Column 19, claim 12,</u>
Line 34, delete "claims 1 to 6" and insert therefor -- claims 1 to 9 --.

<u>Column 20, claim 14,</u>
Line 6, delete "(W)" and insert therefor -- (R') --.
Line 9, delete "R'<0.2D" and insert therefor -- R'>0.2D --;
Line 10, delete "35°$\geq$v$\geq$55°" and insert therefor -- 35°$\leqq$v$\leqq$55° --.

This certificate supercedes Certificate of Correction issued June 26, 2001.

Signed and Sealed this

Twelfth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,036,491
DATED : March 14, 2000
INVENTOR(S) : Hansson

Page 1 of 1

It is certified that error appears in the above-identified patent and that said Letters Patent is hereby corrected as shown below:

Column 19,
Line 25, delete "37" and insert therefor -- $37°$ --.

Column 19, claim 12,
Line 34, delete "claims 1 to 6" and insert therefor -- claims 1 to 9 --.

Column 20, claim 14,
Line 6, delete "(W)" and insert therefor -- (R') --;
Line 9, delete "R'<0.2D" and insert therefor -- R'>0.2D --;
Line 10, delete "$35° \geq v \geq 55°$" and insert therefor -- $35° \leq v \leq 55°$ --.

This certificate supercedes Certificates of Correction issued June 26, 2001 and March 12, 2002.

Signed and Sealed this

Twenty-fifth Day of June, 2002

Attest:

JAMES E. ROGAN
Attesting Officer          Director of the United States Patent and Trademark Office